United States Patent [19]

Sarstedt

[11] 4,004,575
[45] Jan. 25, 1977

[54] APPARATUS FOR LOADING BLOOD EXTRACTING DEVICES

[75] Inventor: Walter Sarstedt, Numbrecht, Rommelsdorf, Germany

[73] Assignee: Walter Sarstedt Kunststoff-Spritzgusswerk, Nuembrecht, Rommelsdorf, Germany

[22] Filed: Mar. 27, 1975

[21] Appl. No.: 562,613

[30] Foreign Application Priority Data

Apr. 2, 1974 Germany .................. 2415835

[52] U.S. Cl. .................. 128/2 F; 128/DIG. 5; 128/278
[51] Int. Cl.² .................. A61B 5/14
[58] Field of Search .......... 128/2 F, DIG. 5, 276, 128/278, 218 A, 218 C, 27 BH

[56] References Cited

UNITED STATES PATENTS

| 2,699,784 | 1/1955  | Krayl       | 128/333   |
|-----------|---------|-------------|-----------|
| 3,018,779 | 1/1962  | Tyler et al.| 128/278   |
| 3,406,684 | 10/1968 | Tsujino     | 128/173 H |
| 3,433,216 | 3/1969  | Mattson     | 128/2 F   |
| 3,656,472 | 4/1972  | Moura       | 128/DIG. 5|
| 3,688,765 | 9/1972  | Gasaway     | 128/173 H |
| 3,885,549 | 5/1975  | Green       | 128/2 F   |
| 3,886,928 | 6/1975  | Sarstedt    | 128/2 F   |

FOREIGN PATENTS OR APPLICATIONS 1,179,487  1/1970  United Kingdom ........ 128/2 F
1,314,765  4/1973  United Kingdom ........ 128/2 F Primary Examiner—Kyle L. Howell
Attorney, Agent, or Firm—Behr & Woodbridge

[57] ABSTRACT

A pneumatic apparatus is employed to automatically load blood extracting devices. The apparatus includes a cylinder and a piston slidably receivable therein. The piston is connected to a casing or housing which supports a blood extracting device. The cylinder may be partially evacuated by forcing it into the housing. Once evacuated the cylinder is maintained in the biased position by a locking lever. The cylinder may be connected either to a blood receiving vessel or to a piston receivable within the blood receiving vessel through which the blood may be extracted. In order to extract blood the extracting device is first positioned in the vein of a patient in the conventional manner. The locking lever is then released and the partial vacuum within the cylinder causes the plunger within the blood receiving vessel to draw blood inwardly. A check valve and parallel channel arrangement in the plug at one end of the cylinder serves to slow and control the rate at which the blood is extracted. An abutment means is attached to the piston rod and serves as a final stop thereon. This device is especially convenient in that it can be manipulated with one hand while the other hand is free to perform other necessary functions.

9 Claims, 9 Drawing Figures

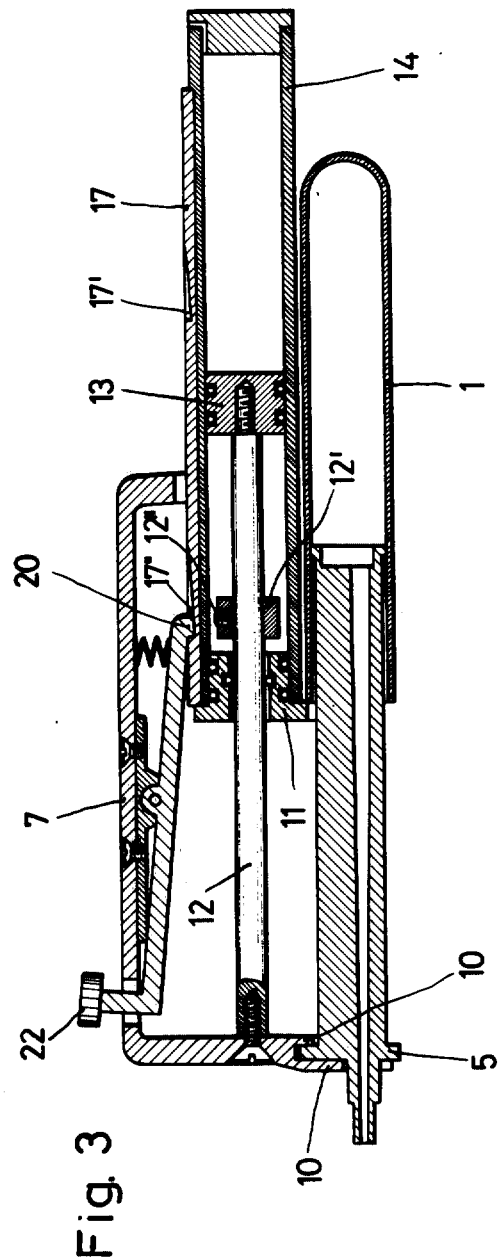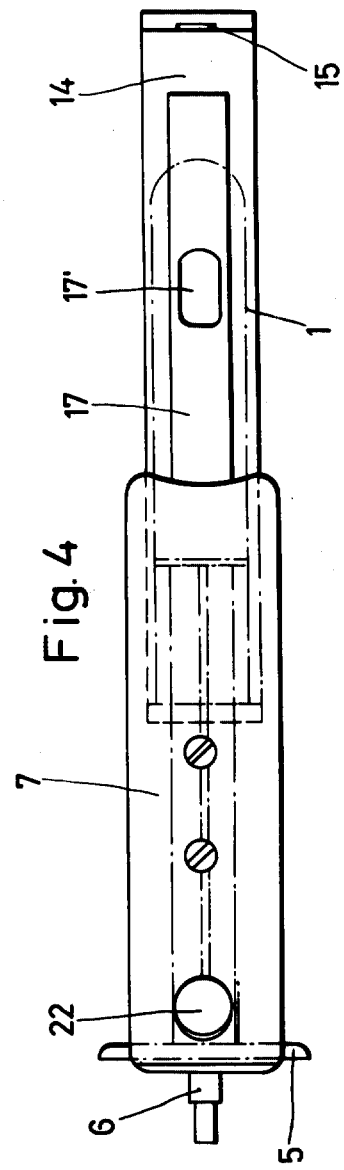

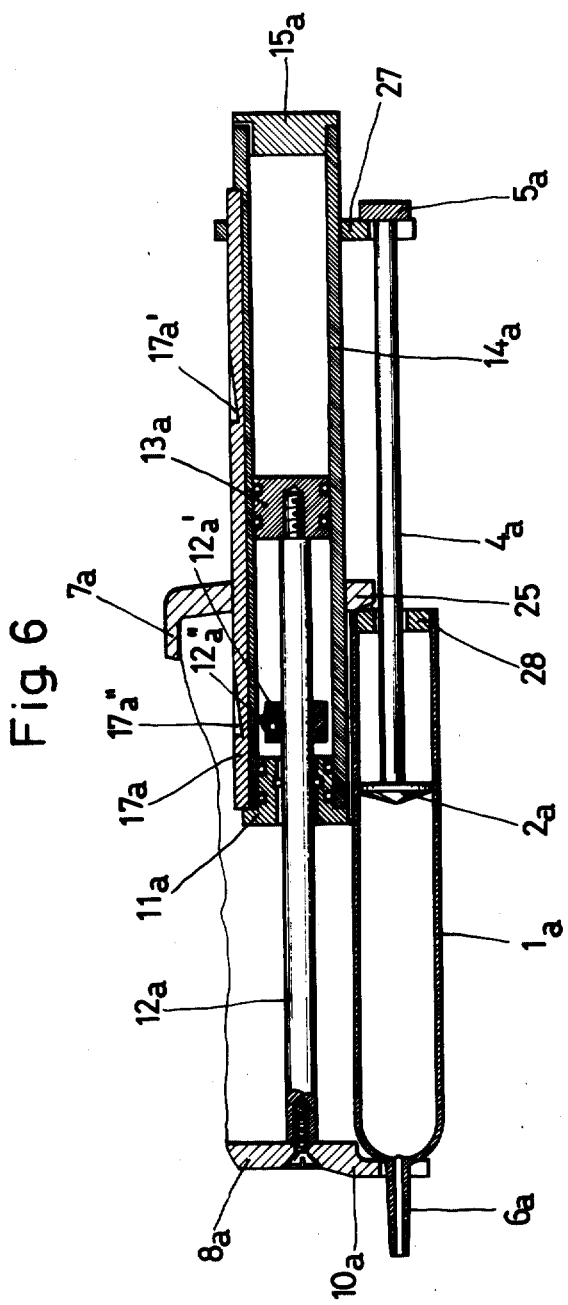

APPARATUS FOR LOADING BLOOD EXTRACTING DEVICES

BACKGROUND OF THE INVENTION

1. Field of the Invention

This invention relates to blood extracting devices.

2. Description of the Prior Art

Various methods and devices are known to those of ordinary skill in the art for extracting blood from the vein of a patient. The simplest prior art method requires a cannula which pierces into the vein. The blood flows out of the other end of the cannula and is collected in a vessel. This method does have the advantage that the blood flows freely and without a loading by a subatmospheric pressure with a relatively low flow velocity. On the other hand this method does have the disadvantage that the vein must be dammed excessively by strangulating, and this actually is not desired. A further disadvantage of this method is that the operation is quite unclean, since it generally is not possible to completely connect the blood flowing from the other end of the cannula, so that the patient's dress or the bed-clothes is contaminated with blood.

According to another prior art method, blood is extracted by means of a conventional injection syringe, and this is done by introducing the cannula applied thereto into the vein and by retracting the piston in the cylinder of the syringe. In this method or use of this device an extensive damming is not necessary and a damming of the blood even is superfluous. On the other hand the high vacuum in the syringe cylinder resulting by a quick retraction is detrimental, since the blood may form and is damaged in its colloidal structure. Also a high flow velocity of the blood in the cannula results, when the retraction is carried out too quickly, and this may result in a hemolysis by the turbulence caused thereby.

A further disadvantage is that after piercing the cannula point into the vein both hands are required for loading the syringe. When doing so a damaging of the opposite vein wall may result by the cannula point when the operation is carried out impatiently or when the patient is impatient.

Finally, the loading of a syringe, in particular with narrow cannulas, requires a certain effort which is tiring for weaker persons and again may result in impatience and thus an injury of the vein wall.

Since sometimes devices have also been used for extracting blood in which the attachment socket for applying the cannula is not secured to one end of the cylinder like in the foregoing mentioned injection syringes, but to the piston rod provided with a continuous longitudinal bore, that piston rod being connected to the piston likewise containing a through-bore, while the cylinder is defined as a tubule closed at one side which may subsequently be used for centrifuging the extracted blood. Although with such a device when extracting blood an excessively high vacuum does not result readily in the receiving cylinder, because this device is easier to manipulate and permits a more sensitive operation, depending on circumstances a high vacuum and a high flow velocity may result by a quick manipulation. With this device both hands are also needed for extracting the blood.

The foregoing mentioned two blood extraction devices would be at an optimum if it would be successful to eliminate the disadvantages of the manipulation with both hands and the disadvantages resulting by a hurried handling.

Now apparatus has become known for loading the foregoing mentioned blood extracting devices, wherein spring means withdraw the piston of the blood extracting device partially from the cylinder thereof upon being relieved. A helical compression spring is used as spring mean's. This spring is initially biased and is released after the cannula of the blood extracting device has been introduced in the vein, so that the spring relieves and loads the blood extracting device. This conventional apparatus has the major disadvantage that the force of the biased spring is very high and accordingly moves the piston of the blood extracting device joltingly in the moment of releasing and in doing so causes an undesired subatmospheric pressure pulse which damages the blood extracted and might even result in a foaming thereof.

In another conventional apparatus for loading blood extracting devices a small electric motor is used which is driven by a battery disposed in the apparatus. This apparatus is extremely complicated and thus on the one hand costly, on the other hand prone to defects and has a weight which renders difficult its operation.

SUMMARY OF THE INVENTION

The invention is based on the problem of providing an apparatus for loading blood extracting devices which does not have the foregoing mentioned disadvantages and which is particularly simple in its structure, cheap in the production and easy in manipulation as well as of a low weight. The object of this apparatus, furthermore, avoids a jolting movement of the piston at the beginning of the loading movement and thus a damaging of the blood extracted.

The solution of this problem is effected according to the present invention by an apparatus associated with the blood extracting device which performs the loading of this blood extracting device automatically, i.e. thereby replaces the manual operation.

In the apparatus according to the invention two parts are provided shiftable relative to one another in longitudinal direction of the blood extracting device, of which one part is able to be connected to the container and the other to the piston rod of the blood extracting device, as well as spring means arranged between these parts and shifting them relative to one another.

These spring means are formed as a pneumatically acting cylinder with a piston according to the invention, said piston initially being withdrawn thereby producing a sub-atmospheric pressure in the cylinder. The piston is retained in this position by locking means and is retracted into the cylinder again upon releasing thereof and in doing so loads the blood extracting device.

The apparatus according to the invention is connected to the two parts of the blood extracting device and is brought into a position in which the spring means are biased, i.e. the piston is withdrawn. Then the locking means are released, and the sub-atmospheric pressure in the cylinder of the apparatus according to the invention causes a slow, jolt-free loading of the blood extracting device.

Since the blood extracting device and the operating apparatus according to the invention define a unit after being connected together, which may be held in one hand, the blood extraction can be effected completely with one hand, while the other hand e.g. holds tight the patient's arm.

By an appropriate selection of the maximum subatmospheric pressure the speed with which the blood extracting device is loaded may be limited to an acceptable value.

By suitable dimensioning of the cylinder serving as spring means together with the piston and the determination of its two limit positions the force with which the blood extracting device is loaded decreases only slightly during the stroke of the piston. Therefore, a flow velocity will be obtained depending on the diameter and the length of the cannula and according to the viscosity of the blood which remains relatively constant over the major part of the stroke. Consequently at the beginning of the blood extraction there will be no excessively high flow velocity and no foaming or any other damaging of the blood extracted.

The releasable locking means may be defined in any desired way, provided it permits an easy releasing of the two parts in the biased position of the spring means. Preferably, however, there are two provisions that a saw-tooth-like detent groove is provided at the cylinder periphery and a ratchet releasably engaging in the detent groove is provided, said ratchet being connected through a bale to the piston rod. This brings about the advantage that the blood extraction may be initiated after introducing the cannula into the vein by a simple pressure on an operating knob connected to the ratchet and that in doing so no vibrations are caused which could result in an injury of the vein by the tip of the cannula.

Furthermore, it is proposed to provide a stationary or adjustable, possibly releasable abutment for the movement of the manipulation apparatus which then terminates the loading of the blood extracting device at a specific stroke and thus at a specific blood volume. The operator then does not have to observe carefully anymore the movement of the apparatus.

Preferably the bale carrying the engaging ratchet at the same time is a retaining handle and a casing for the apparatus.

The apparatus according to the invention thus permits a convenient one hand manipulation and a slow, safeguarding extraction of the blood.

Possibly the apparatus may also be provided with a brake operable manually, said brake permitting a reduction of the loading velocity or a termination of the movement in any desired position.

Preferably a check valve is provided in the closure plug of the cylinder of the manipulation apparatus for an easier biasing of the apparatus, said check valve permitting an easy escaping of air but closing during the later relieving. The air then must flow through a channel in the plug during the relieving process, the passage opening of said channel being adjustable.

In this context preferably a disk is provided having axial bores of various width, arranged at the external face of the plug and rotatable relative thereto, the openings of which are selectively capable of being brought in register with the longitudinal bore of the plug.

This brings about the possibility of influencing the loading velocity and to adapt it to various blood extracting devices.

Furthermore, it is proposed according to the invention to arrange a second saw-tooth-like detent groove on the periphery of the cylinder, which is associated to the foregoing mentioned ratchet and which terminates the loading movement shortly in advance of the end position determined by the abutment. This permits a starting of the loading movement initially by a first manipulation of the locking ratchet, and to terminate it slightly in advance of the end position by an engagement of the locking ratchet in the second detent groove. A renewed releasing of the locking ratchet simultaneously with the removal of the cannula from the vein or shortly thereafter then causes a slight residual stroke which has as a result that the small amount of blood in the cannula likewise is drawn into the blood extracting device and is not able to drop out of the point of the cannula again e.g. by result of heat expansion. This thus permits a clean operation, and this is of a great advantage in particular when extracting infectious blood.

The invention is explained in closer detail hereinafter by way of examples in referring to the drawings. In the drawings:

BRIEF DESCRIPTION OF THE DRAWINGS

FIG. 3 is a sectional view of the apparatus of FIG. 1, but in the loaded, relieved condition;

FIG. 4 is a plan view of the apparatus in the position according to FIG. 3;

FIG. 6 is a sectional view of the apparatus of FIG. 5, but in the loaded, relieved condition;

DETAILED DESCRIPTION OF THE INVENTION

Figure 1:
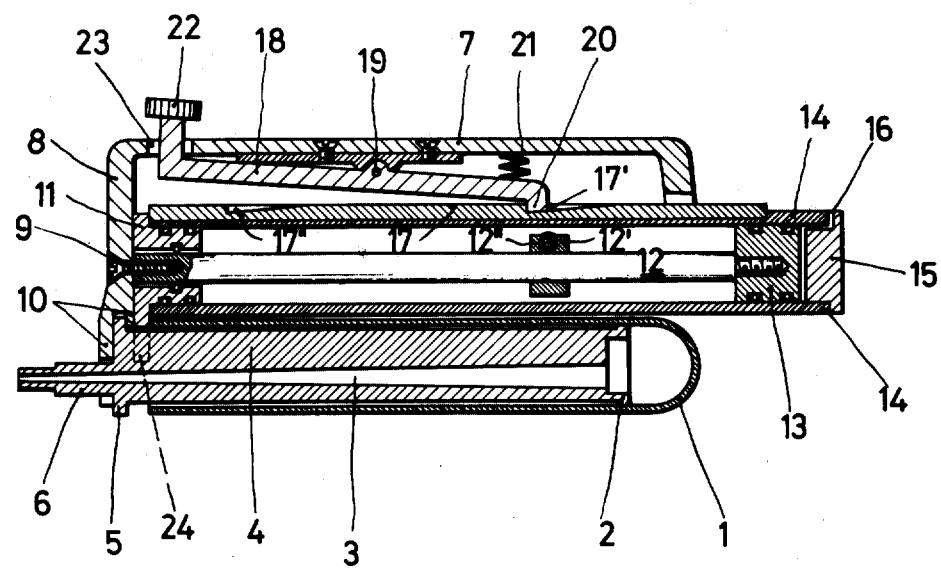
FIG. 1 is a sectional view of an apparatus according to the invention with an applied blood extracting device in the biased condition.
Figure 2:
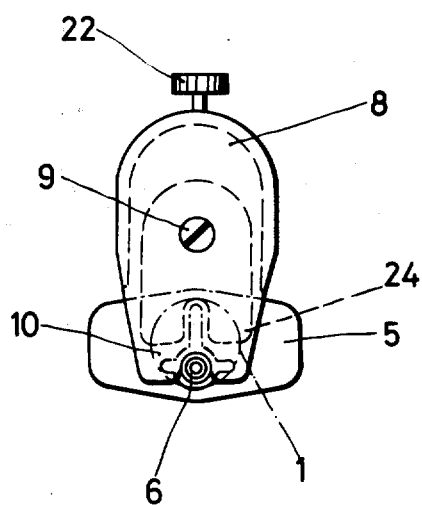
FIG. 2 is a plan view of the front side of the apparatus (left-hand side in FIG. 1)

The apparatus illustrated in FIGS. 1 to 4 includes a casing 7 at the same time serving as a grip, at the face 8 of which a piston rod 12 is attached extending parallel to the casing 7, by means of a screw 9, said piston rod having a piston 13 secured to the end thereof. The piston is disposed in a cylinder 14 which is closed at its left-hand end closed in FIG. 1 by a plug 11 which has a central bore and is shiftable therewith sealed on the piston rod 12.

At the other end (right-hand side in FIG. 1) the cylinder 14 is closed by a plug 15 which has a lateral bore 16 through which the air may flow drawn in or pressed out when the piston 13 is shifted within the cylinder 14.

On the cylinder 14 at the top side a rod 17 is secured provided with two detents 17' and 17''. In each of these two detent grooves formed saw-tooth-like the lobe 20 at the end of a two-armed lever 18 pivoted at 19 may engage which is urged by a spring 21 with the lobe 20 against the tooth rod 17, but which may be released in counteraction to the force of this spring by de-pressing the hand knob 22. The hand knob 22 is secured to the bent end of the two-armed lever 18 which extends through a bore 23 in the casing 7.

The front plate 8 of the casing 7 carries a retainer at the bottom side comprising two prongs 10 into which the handle piece 5 of a blood extracting device may be inserted. This handle piece is secured to the front end of the winged piston 4 and carries an attachment piece 6 for receiving a cannula. At the end of the piston rod which has a tapered longitudinal bore 3 there is a piston 2 which is slidable hermetically sealed in the tubule 1 serving as a cylinder and closed at one side.

A finger 24 depends from the closure plug 11 of the manipulating apparatus, which engages the rim of the tubule 1, as is shown in FIG. 1. The finger 24 is provided with a slot in which the upper wing of the piston 4 is freely shiftable.

FIG. 1 shows the apparatus in the biased position in which a vacuum has been produced in the cylinder 14 by shifting the piston 13 in this cylinder, said vacuum tending to shift the cylinder to the right in relationship to the piston.

FIG. 3 shows the almost completely relieved retracted position of the apparatus in which there is only a low sub-atmospheric pressure in the left-hand part of the cylinder 14 between the two pistons 11 and 13. In this position the blood extracting device is loaded; as is noted, the FIG. 24 at the plug 11 has displaced the tubule 1 relative to the piston 2 to the right, or the handle piece 5 of the piston rod is retained by the retaining fingers 10.

There is an abutment ring 12' on the piston rod 12, as illustrated in FIGS. 1 and 3, said abutment ring being shiftable along said piston rod and being secured on the piston rod in a predetermined position by means of an adjusting screw 12" radially extending through the ring. As will be noted from FIG. 3, the abutment ring 12' is secured to the piston rod 12 in such a position that it has only a slight spacing of only a few millimeters from the bored piston 11 guiding the piston rod when the lobe 20 of the locking ratchet 18 engages in the second detent groove 12" at the left-hand end of the rod 17. When now by depressing the knob 22 the ratch 18 is again pivoted and the lobe 20 is withdrawn from the detent groove 17", the low subatmospheric pressure still prevailing in the cylinder 14 at the left-hand side of the piston 13 draws the cylinder 14 to the right by a slight extent until the ring 12' engages the piston 11 and thereby finally terminates the loading movement. Thereby, the blood extracting device is loaded further and draws a further slight amount of blood. When practically using the apparatus this last small stroke is released by a renewed depressing of the knob 22 when extracting the cannula from the vein or shortly thereafter so that the blood in the cannula is drawn into the tubule 1 by the residual stroke.

The blood extracting device, comprising the tubule 1 and the piston 2 with the piston rod 4 and the applied cannula can now readily be removed from the apparatus according to the invention downwardly.

In the modified embodiment of the manipulation apparatus illustrated in FIGS. 5 to 8 the fingers are arranged differently for loading the blood extracting device in order to permit the loading of another conventional blood extracting device. This blood extracting device comprises a syringe cylinder 1a with a piston 2a shiftable hermetically sealed therein and being secured to the left-hand end of a piston rod 4a. This piston rod is guided loosely mechanically in the ring 28 which is fitted into the end of the cylinder 1a, and it carries a grip piece 5a at its outer end. The syringe cylinder 1a is bored at its left-hand end and is connected to an attachment piece 6a for applying a cannula.

The manipulation apparatus for loading this blood extracting device differs from the manipulation apparatus according to FIGS. 1 to 4 by a different arrangement of the retaining fingers, while all other parts are essentially unmodified and, therefore, have been assigned the same reference numerals in adding the index a.

The retaining finger 10a here receives the attachment piece 6a of the syringe cylinder 1a in a slot open to the bottom. A further retaining of the syringe cylinder 1a is effected, as is perceivable in particular from FIG. 7, by the retaining plate 25 projecting downwardly from the casing 7a with bent retaining springs 26 attached thereto.

Furthermore, a plate 27 projects from the cylinder 14a of the manipulation apparatus provided with a slot at the lower end, said plate receiving the end of the piston rod 4a in the slot and engaging behind the grip piece 5a of this piston rod.

When relieving the manipulation apparatus this plate 27 then moves the grip piece 5a of the piston rod 4a and thus the piston 2a to the right and thereby loads the syringe, as will be noted from FIG. 6.

In this embodiment of the manipulation apparatus according to the invention a ring 12a' is likewise secured to the piston rod 12a, which, as will be noted from FIG. 6, still has a slight spacing from the piston 11a when the lobe of the ratchet engages in the left hand detent groove 17a". For the sake of simplicity the left-hand detent groove 17a" has been illustrated in FIG. 6 only, but not the lobe of the ratchet which engages in the left-hand detent groove 17a" in this position of the apparatus. The conditions, however, are otherwise completely equivalent to those which have been illustrated for the other embodiment in FIG. 3.

Figure 5:
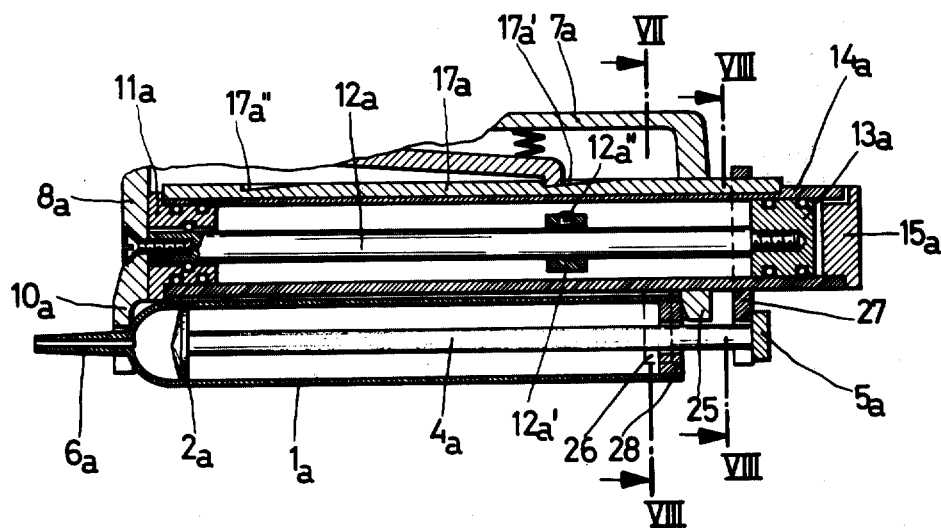
FIG. 5 is a partially broken away sectional view of another embodiment of the apparatus according to the invention.
Figure 7:
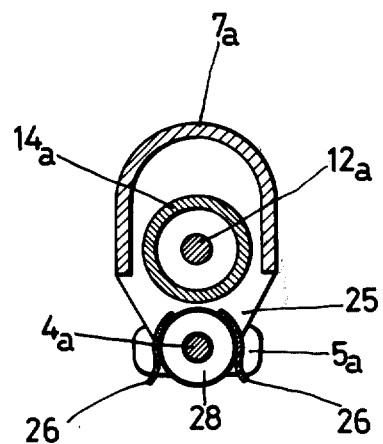
FIG. 7 is a sectional view taken along line VII—VII of FIG. 5.
Figure 8:
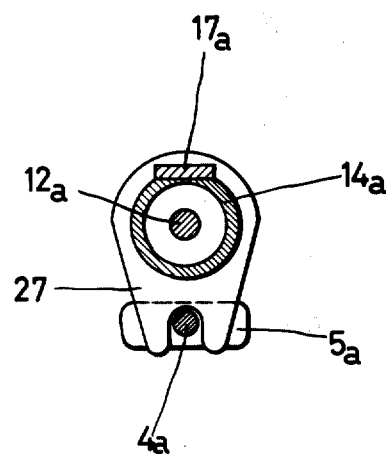
FIG. 8 is a sectional view taken along line VIII—VIII of FIG. 5.
Figure 9:
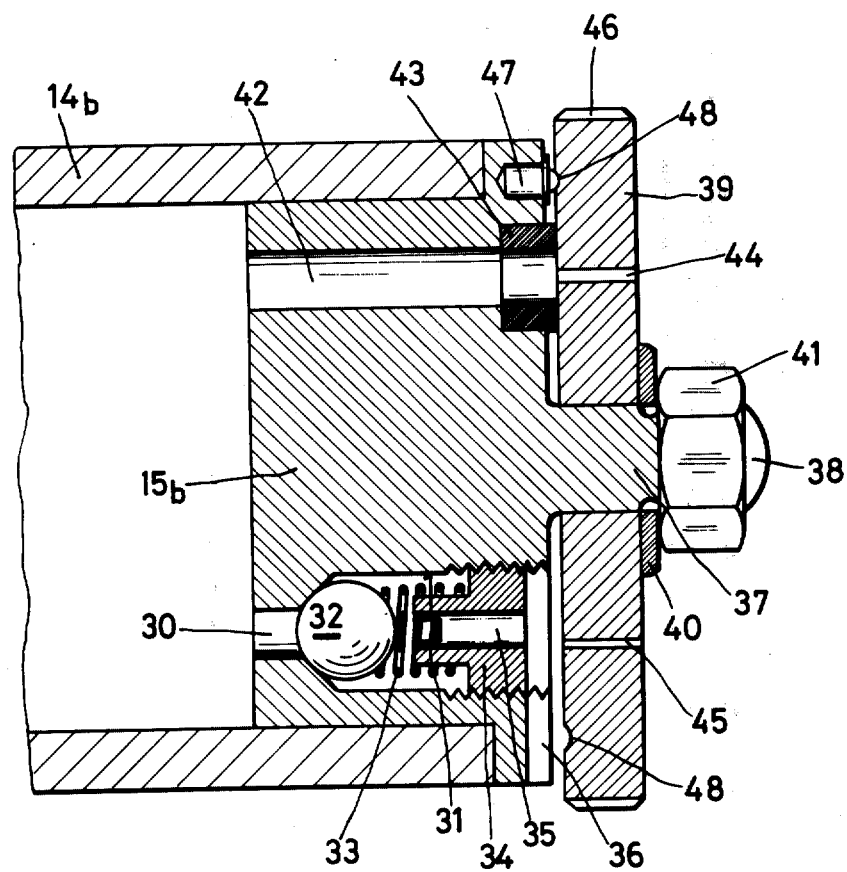
FIG. 9 is an enlarged sectional view of a closure plug in the cylinder of the manipulation apparatus, with a check-valve and an adjustable inlet opening.

Instead of the plug 15 or 15a illustrated in FIGS. 1, 3 and 4 or in the other embodiment in FIGS. 5 and 6, said plug closing the right-hand end of the cylinder of the manipulation apparatus and having a channel for the flowing in and out of air, preferably the closure plug illustrated in FIG. 9 is used. This plug 15b which is tightly fitted into the end of the cylinder 15b has an excentric bore 30 parallel to the axis which is enlarged for receiving a check valve in the part 31 and is closed by a screwed-in plug 34. The check valve comprises a ball 32 and a helical compression spring 33. The plug 34 is bored and opens in a radially extending channel 36 in the outer face of the plug 15b. When for biasing the apparatus the cylinder 14b is moved to the left with the plug 15b and is pushed over the piston, the air in the cylinder between the piston and the plug 15b is compressed. Thereby, the check valve is opened, and the air escapes through the bore 30, the enlarged part 31, the bore 35 in the plug 34 and the channel 36 to atmosphere. Since the bores and channels are dimensioned accordingly large, there are no difficulties in winding up the apparatus.

Upon relieving a subatmospheric pressure results in the right-hand part of the cylinder of the manipulation apparatus, however, and the check valve remains closed. There is now a second bore 42 parallel to the axis in the plug 15b, the outer opening of said bore being surrounded by an annular seal 43.

The plug 15b, furthermore, has a spigot 37 projecting axially outwardly and having an offset end carrying threads.

The spigot 37 carries a disk 39 freely rotatable which projects beyond the cylinder 14b in radial direction slightly and is provided with riffling 46 at its periphery. The disk 39 is urged by a nut 41 through the intermediary of a disk 40 against the face of the plug 15b and in particular against the seal 43 and sealingly engages the face of this seal.

The rotatable disk 49 is provided with a plurality of circumferentially spaced bores of various diameters, of which one bore 44 has been illustrated in FIG. 9, in register with the opening of the seal 43 and the bore 42 in alignment therewith, while a second, slightly narrower bore 45 has been illustrated in the lower part of the disk 39 illustrated in FIG. 9.

When relieving the manipulation apparatus, a subatmospheric pressure is produced in the right-hand part of the cylinder 14b, as has been mentioned already, said sub-atmospheric pressure tending to balance through the bore 44 and the adjacent bore 42. Depending on the diameter of the bore which has been brought in register with the bore 42 by rotation of the disk 39, the flowing of air inwardly is restricted more or less and thereby the loading movement of the manipulation apparatus is braked in a specific fashion. Thereby the manipulation apparatus can be adapted to blood extracting devices of various sizes as well as also to various blood viscosities, namely by rotating the disk 39 into the desired position. A ball snap 47 is provided for arresting these positions, various recesses 48 in the disk 39 being complementary to the positions of the bores.

What is claimed is:

1. An apparatus for loading blood extracting devices comprising:
    a casing means;
    a pneumatic means connected to said casing means and adapted to assume a manually biased, partially evacuated state and an unbiased less evacuated state;
    a locking means for locking said pneumatic means in said biased partially evacuated state; and,
    a blood extracting device attached to said casing means and to said pneumatic means and adapted to extract blood when said pneumatic means moves from said biased state to said unbiased state.

2. The apparatus of claim 1 wherein said pneumatic means includes a piston means rigidly connected to said casing and a cylinder for slidably receiving said piston means.

3. The apparatus of claim 2 wherein said cylinder includes a plurality of locking detents therein; and,
    said locking means comprises a releasable lever means pivotally attached to said casing means and adapted to engage one of said locking detents when said pneumatic means is in said biased state.

4. The apparatus of claim 2 further comprising:
    a plug situated in one end of said cylinder, said plug including a slowing means therein for controlling the movement of said pneumatic means.

5. The apparatus of claim 4 wherein said slowing means comprises:
    a check valve located in a first opening through said plug; and,
    a second opening parallel to said first opening through said plug.

6. The apparatus of claim 5 further comprising:
    a disc rotatably attached to said plug and provided with a plurality of axial bores of various widths therethrough, said bores being adapted for alignment with said second opening in said plug.

7. The apparatus of claim 2 wherein said piston comprises a piston rod and a head connected together, said rod including an abutment means thereon for limiting the movement of said pneumatic means.

8. The apparatus of claim 7 wherein said abutment means comprises a ring adapted to abut against one end of said cylinder.

9. The apparatus of claim 3 wherein said cylinder includes at least a first and a second locking detent therein and wherein said second detent is adapted to engage said locking means in advance of the point at which said abutment ring makes contact with one end of said cylinder.

* * * * *